(12) United States Patent
Paoli et al.

(10) Patent No.: US 12,377,213 B2
(45) Date of Patent: Aug. 5, 2025

(54) MEDICAL DEVICE COMPRISING AN ACTUATION ELEMENT

(71) Applicant: Fresenius Vial SAS, Brézins (FR)

(72) Inventors: Mathieu Paoli, La Murette (FR); Damien Archat, Grénoble (FR); Fabien Thomas, Saint Victor de Cessieu (FR); Jean-Marc Ulrich, Saint Jean de Moirans (FR)

(73) Assignee: Fresenius Vial SAS, Brézins (FR)

( * ) Notice: Subject to any disclaimer, the term of this patent is extended or adjusted under 35 U.S.C. 154(b) by 820 days.

(21) Appl. No.: 17/270,373

(22) PCT Filed: Sep. 24, 2019

(86) PCT No.: PCT/EP2019/075694
§ 371 (c)(1),
(2) Date: Feb. 22, 2021

(87) PCT Pub. No.: WO2020/078675
PCT Pub. Date: Apr. 23, 2020

(65) Prior Publication Data
US 2021/0316067 A1 Oct. 14, 2021

(30) Foreign Application Priority Data
Oct. 19, 2018 (EP) .................................... 18306375

(51) Int. Cl.
*A61M 5/172* (2006.01)
(52) U.S. Cl.
CPC .................................. *A61M 5/172* (2013.01)
(58) Field of Classification Search
CPC .. A61M 2205/8275; A61M 2005/2026; A61M 2005/14506; H01H 2019/143;
(Continued)

(56) References Cited

U.S. PATENT DOCUMENTS 5,271,293 A 12/1993 Olsson et al.
10,535,478 B1* 1/2020 Chu ....................... H01H 9/181
(Continued)

FOREIGN PATENT DOCUMENTS

CN 101825913 9/2010
CN 102725019 10/2012
(Continued)

OTHER PUBLICATIONS

Office Action and Search Report (with English-language translation), counterpart Chinese App. No. 201980068270.7 (Jan. 18, 2023) (21 pages).
(Continued)

*Primary Examiner* — Courtney B Fredrickson
*Assistant Examiner* — Kayla M. Turkowski
(74) *Attorney, Agent, or Firm* — Cook Alex Ltd.

(57) ABSTRACT

A medical device (1) for administering a medical fluid to a patient (4) comprises a housing (10) comprising a housing portion (11), a control device (19) for controlling operation of the medical device (1), a control element (18) placed on said housing portion (11) and being actuatable for entering a control command to be input to the control device (119), wherein the control element (18), for actuation, is at least one of rotatable about an axis of rotation (R) and linearly movable along the axis of rotation (R) with respect to said housing portion (11), and an actuation element (15) operatively connected to the control element (18) for actuating the control element (18). Herein, the actuation element (15) comprises a first knob element (17) operatively connected to the control element (18) and a second knob element (16) supported on said housing portion (11).

19 Claims, 4 Drawing Sheets

(58) Field of Classification Search
CPC .... H01H 19/003; H01H 13/585; H01H 17/24; H01H 17/18; H01H 2019/008; H01H 2025/048; G05G 5/12; G05G 5/04; G05G 1/10

See application file for complete search history.

(56) References Cited

U.S. PATENT DOCUMENTS

| | | | |
|---|---|---|---|
| 2008/0289940 A1* | 11/2008 | Kim | H01H 19/02 200/336 |
| 2009/0202319 A1 | 8/2009 | Wang et al. | |
| 2009/0301852 A1* | 12/2009 | Keist | B60K 35/10 200/341 |
| 2010/0084249 A1 | 4/2010 | Bandy et al. | |
| 2010/0177494 A1* | 7/2010 | Kim | D06F 34/30 361/837 |
| 2011/0172601 A1 | 7/2011 | Beebe et al. | |
| 2012/0179142 A1 | 7/2012 | Abal | |
| 2013/0037392 A1* | 2/2013 | Nakajima | G05G 1/08 200/9 |
| 2013/0317431 A1* | 11/2013 | KraMer | A61M 5/5086 604/131 |
| 2014/0039310 A1* | 2/2014 | Suchecki | A61M 5/14216 600/432 |
| 2014/0208251 A1 | 7/2014 | Houde et al. | |
| 2015/0051571 A1 | 2/2015 | Lanigan et al. | |
| 2016/0045665 A1* | 2/2016 | Bayer | A61M 5/315 604/207 |
| 2017/0203034 A1 | 7/2017 | Lee | |
| 2019/0051468 A1* | 2/2019 | Turner | G05G 1/12 |
| 2021/0187217 A1* | 6/2021 | Landwehr | A61M 16/024 |

FOREIGN PATENT DOCUMENTS

| | | |
|---|---|---|
| CN | 105102017 | 11/2015 |
| CN | 205041889 | 2/2016 |
| CN | 106714875 | 5/2017 |
| CN | 107300946 | 10/2017 |
| CN | 107624075 | 1/2018 |
| EP | 3085404 | 10/2016 |
| WO | WO 2017/021531 | 2/2017 |
| WO | WO 2017/032498 | 3/2017 |

OTHER PUBLICATIONS

International Search Report and Written Opinion, counterpart International Appl. No. PCT/EP2019/075694 (Oct. 22, 2019) (10 pages).

Office Action and Search Report (with English-language translation), counterpart Chinese App. No. 201980068270.7 (Sep. 4, 2023) (24 pages).

* cited by examiner

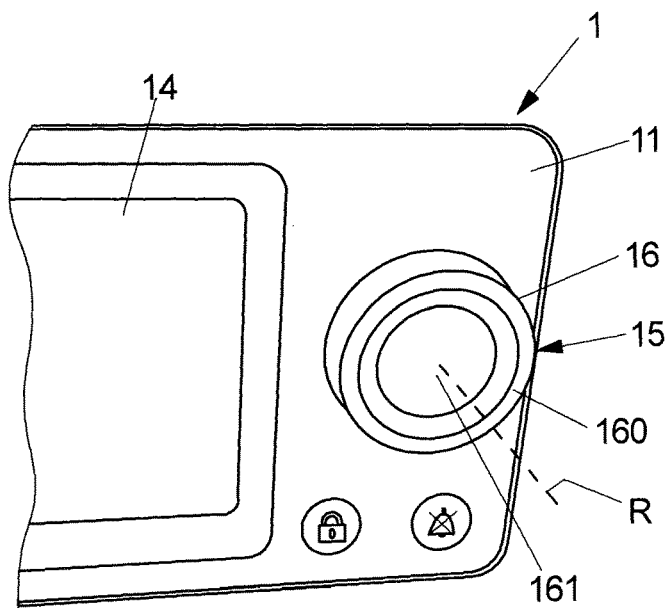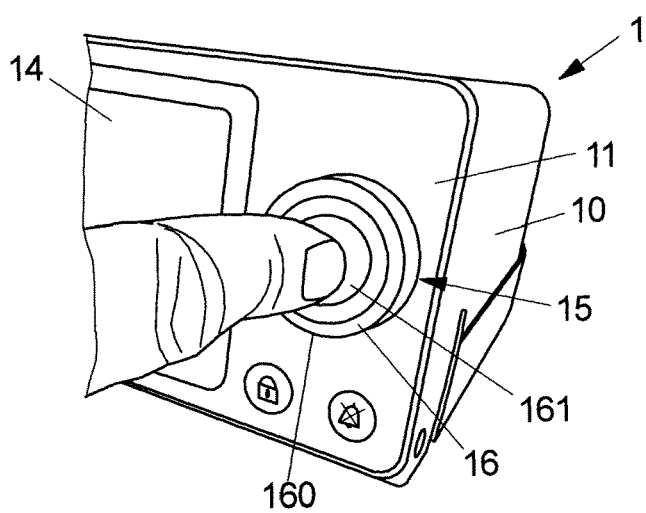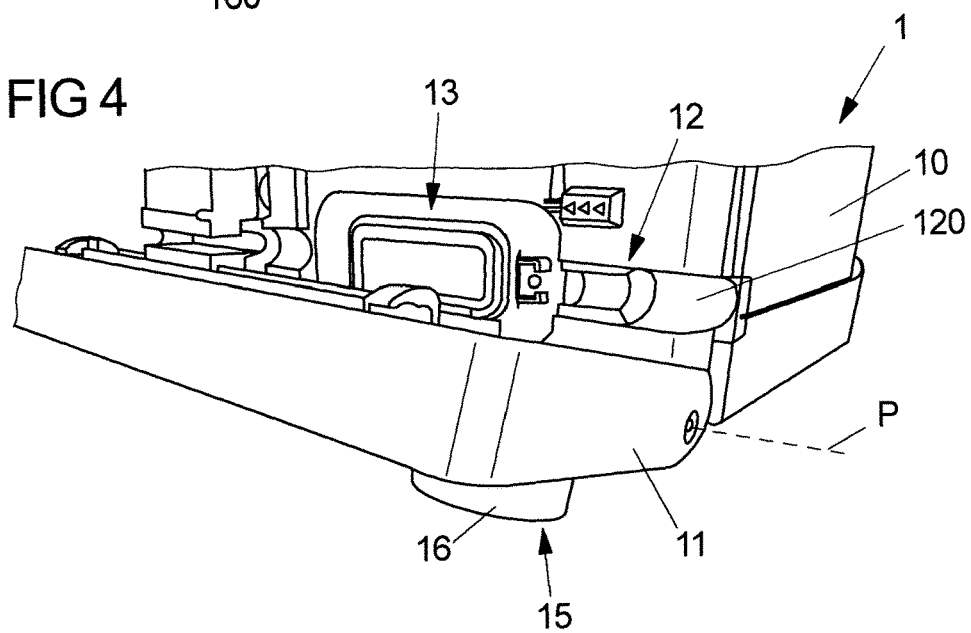

FIG 8
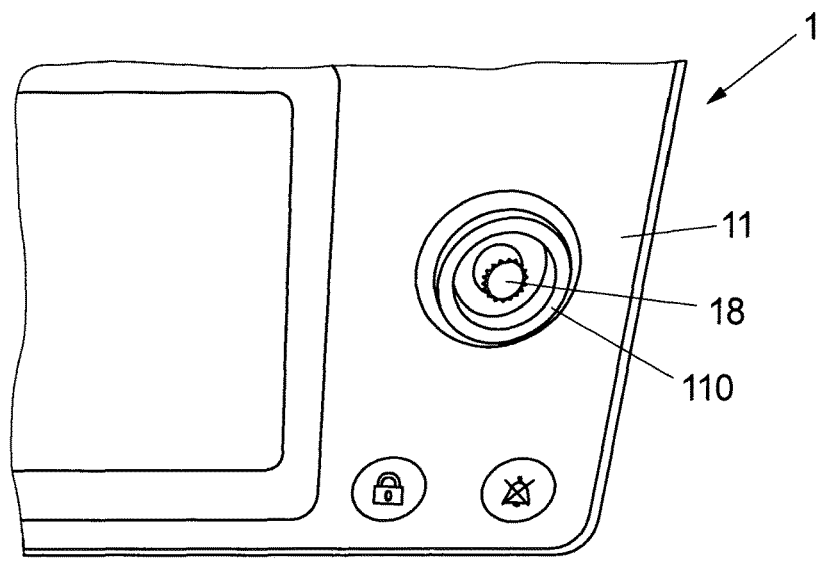
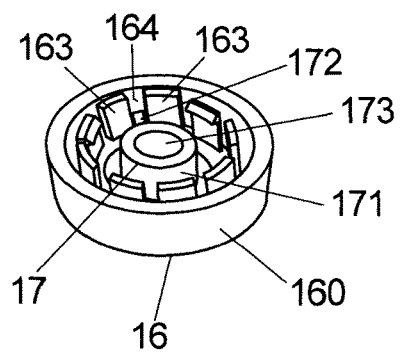
FIG 9
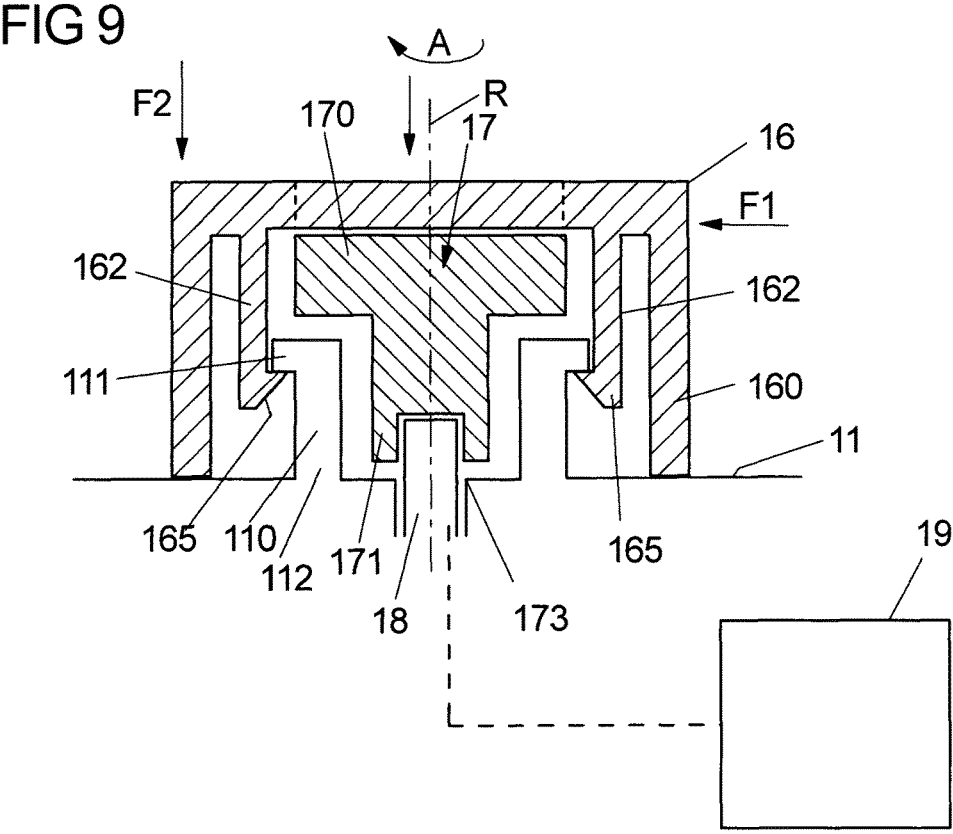

MEDICAL DEVICE COMPRISING AN ACTUATION ELEMENT

The present application is a U.S. National Stage of PCT International Patent Application No. PCT/EP2019/075694, filed Sep. 24, 2019, which claims priority to EP Application Serial No. 18306375, filed Oct. 19, 2018, both of which are hereby incorporated herein by reference.

The invention relates to a medical device for administering a medical fluid to a patient according to the preamble of claim 1.

A medical device of this kind, for example an infusion device, comprises a housing having a housing portion and a control device for controlling operation of the medical device. A control element is placed on said housing portion and is actuatable for entering a control command to be input to the control device, wherein the control element, for actuation, is at least one of rotatable about an axis of rotation or linearly movable along the axis of rotation with respect to said housing portion. In addition, the medical device comprises an actuation element which is in operative connection with the control element and serves to actuate the control element.

A medical device of this kind, for example an infusion device, is for example placed at the bedside of a patient, for example together with other medical devices on a rack serving to hold a multiplicity of medical devices in an organized fashion at the bedside of the patient. The medical device for example may be constituted by a volumetric (peristaltic) infusion pump or a syringe infusion pump. In case of a volumetric infusion pump, a pumpset can be placed in a receptacle formed on the housing such that the pumpset comes into operative connection with a pumping mechanism of the infusion device, the pumping mechanism configured to act onto the pumpset for delivering a medical fluid through the pumpset towards a patient to which the pumpset is connected. In case of a syringe infusion pump, a syringe can be placed within a receptacle of the infusion pump such that a pusher device comes into operative connection with a piston of the syringe. By means of the pusher device the piston can be pushed into a cylindrical tube of the syringe such that a fluid may be delivered from the syringe towards a patient.

The actuation element is placed on the housing portion, for example a closure element in the shape of a door of the medical device, and generally is connected to the control element such that a user may act onto the actuation element for actuating the control element. The actuation element herein can be rotated or pushed, such that a corresponding action is transferred to the control element and hence the control element is rotated or pushed. By means of such action a control command can be input to the control device, for example to scroll through a menu displayed on a display device of the medical device or to enter a control command, for example by choosing an entry of the menu.

During use of the medical device the actuation element may experience loads and forces, which however shall not cause damage at the control element. It in this regard is desirable that, in case of excessive loads or forces, a damage may occur (if at all) only at the actuation element, but not at the control element, such that in case of damage only the actuation element, but not the control element or any integrated mechanics or electronics of the medical device needs to be replaced.

Despite this, however, a user action for entering a control command shall reliably be transferred to the control device, hence requiring a reliable operative connection between the actuation element and the control element.

A medical device in the shape of an infusion device is for example known from EP 3 341 046 A1.

It is an object of the instant invention to provide a medical device for administering a medical fluid to a patient, the medical device having an actuation element which allows to prevent a transfer of excessive loads and forces to the control element, hence preventing a damage of the control element in case of excessive loads and forces.

This object is achieved by means of a medical device comprising the features of claim 1.

Accordingly, the actuation element comprises a first knob element operatively connected to the control element and a second knob element supported on said housing portion, wherein the second knob element is user actuatable and operatively connected to the first knob element such that a user action is transferred to the first knob element and via the first knob element to the control element for actuating the control element.

The housing portion may for example be a closure element in the shape of a door of the medical device. The closure element may for example be pivotably arranged on a housing body and may be opened to access a receptacle of the medical device.

The medical device may for example be an infusion device, such as a volumetric (peristaltic) infusion pump or a syringe infusion pump. In case of a volumetric infusion pump, a pumpset having an infusion line may be received in a receptacle of the medical device such that a pumping mechanism comes into operative connection with the pumpset and may act onto the pumpset for delivering a medical fluid through the pumpset towards a patient. In case of a syringe infusion pump, a syringe may be received in a receptacle of the medical device such that a pusher device comes into operative connection with the syringe for acting onto the syringe for delivering a medical fluid from the syringe towards a patient.

The actuation element comprises a first knob element and a second knob element. The actuation element hence comprises two parts, which are formed functionally separate from one another.

The first knob element is operatively connected to the control element such that via the first knob element an actuation action may be transferred to the control element for actuating the control element. The second knob element in turn is operatively connected to the first knob element and is user actuatable. The second knob element hence forms an external element which may be accessed by a user for inputting a control command. The second knob element is supported on the housing portion, for example the closure element of the medical device, and hence is seated on the housing portion.

Since the second knob element is user actuatable and represents an external element, loads and forces will act primarily on the second knob element. Because the second knob element is seated on the housing portion, excessive loads and forces may be introduced into the housing portion. Because the second knob element is not directly connected to the control element, but the first knob element is placed in between the second knob element and the control element, forces are not directly transferred from the second knob element to the control element, but a flow path of load forces to the control element may be disrupted, hence preventing a transfer of excessive loads and forces to the control element.

In case of excessive loads and forces a damage hence will likely occur (if at all) only at the second knob element, but not at the control element. In case of a damage, hence, only the second knob element needs to be replaced, but the control element and any mechanics or electronics of the medical device associated with the control element remains unaffected.

The second knob element, in one embodiment, is rotatably mounted on the housing portion. The second knob element hence is connected to the housing portion such that it may be rotated with respect to the housing portion, but at the same time is supported on the housing portion such that forces acting along the axis of rotation or in a plane transverse to the axis of rotation are transferred from the second knob element into the housing portion, but preferably not to the first knob element and not to the control element.

For connecting the second knob element to the housing portion, the second knob element beneficially comprises one or multiple locking elements connecting the second knob element to the housing portion in a positive locking manner. The one or multiple locking elements beneficially are in engagement with a fixation member arranged on the housing portion such that the second knob element is supported with respect to the housing portion along the axis of rotation and in a plane transverse to the axis of rotation, but at the same time is rotatable about the axis of rotation with respect to the housing portion.

The one or multiple locking elements may for example be elastically deformable and may have the shape of clips elements which allow to place the second knob element on the housing portion, under elastic deformation of the one or multiple locking elements, for connecting the second knob element to the housing portion.

In one embodiment, the second knob element comprises a group of multiple locking elements arranged along a circle circumferentially extending about the axis of rotation, the first knob element being received radially inside the group of locking elements. The locking elements hence are placed circumferentially around the first knob element, the locking elements establishing a positive locking connection in between the second knob element and the housing portion such that the second knob element is supported and held on the housing portion. The first knob element herein is placed inside the locking elements and is operatively connected to the second knob element such that an (intentional) actuation of the second knob element causes an actuation of the first knob element and a corresponding actuation of the control element for entering a control command into the medical device.

In one embodiment, the fixation member extends circumferentially about the control element, the control element hence being placed radially within the fixation member. The fixation member may for example be indirectly connected to the housing portion and may comprise a board portion axially protruding from the housing portion and a rim section radially protruding with respect to the wall portion. The rim section serves to establish the positive leg locking connection between the second lock element and the housing portion, one or multiple locking elements of the second knob element being in positive locking connection with the rim section and hence holding the second knob element along the axis of rotation with respect to the housing portion and at the same time supporting the second knob element in a plane transverse to the axis of rotation with respect to the housing portion.

In one embodiment, the second knob element comprises an edge portion by means of which the second knob element is supported on the housing portion. The edge portion for example is in abutment with the housing portion along the axis of rotation, such that loads acting onto the edge portion of the second knob element along the axis of rotation are directly transferred, by means of the abutment, from the edge portion into the housing portion. The edge portion is for example formed by a cylindrical, circumferential outer wall of the second knob element extending circumferentially about the axis of rotation, the second knob element having a generally cylindrical shape and being accessible by a user for actuating the actuation element.

In one embodiment, the second knob element comprises a push portion which for example is formed at a central location of the second knob element radially inside the edge portion. The push portion may for example be formed from a flexible material and hence may be flexibly deformed with respect to the edge portion. A user may press onto the push portion in order to act onto the first knob element (received within the second knob element) and via the first knob element onto the control element, such that the control element is linearly pushed along the axis of rotation for inputting a control command. Because a user may act onto the second knob element only at a specific location (at the push portion), loads and forces acting onto the second knob element at other portions, specifically at the edge portion, are not transferred to the first knob element received within the second knob element, but are transferred from the second knob element to the housing portion, such that such loads and forces may hence not cause damage at the control element.

In one embodiment, the first knob element is operatively connected to the control element such that at least one of a rotational movement about the axis of rotation and a linear movement along the axis of rotation is transferred to the control element to cause a corresponding movement of the control element. For transferring a rotational action, the first knob element for example is arranged on the control element in a rotationally fixed manner. For transferring a pushing action to the control element, the first knob element is connected to the control element such that a pushing action of the first knob element is transferred into a corresponding linear movement of the control element along the axis of rotation.

In one embodiment, the first knob element comprises a head portion and a shaft portion. The shaft portion extends from the head portion along the axis of rotation and serves to establish the connection between the first knob element and the control element. By means of the shaft portion, the first knob element may be connected to the control element in a rotationally fixed manner and/or a translationally fixed manner. The head portion is operatively connected to the second knob element and for this is received within the second knob element such that a (specific, intentional) user actuation of the second knob element is transferred to the first knob element and via the first knob element to the control element.

In one embodiment, the head portion is arranged within the second knob element with a play when viewed along a plane transverse to the axis of rotation. The first knob element hence comprises a play with respect to the second knob element transverse to the axis of rotation. Forces and loads acting onto the second knob element along a direction transverse to the axis of rotation hence are not transferred to the first knob element, but again are diverted from the second knob element into the housing portion. Excessive loads and forces hence are not transferred to the first knob element, hence preventing a damage of the control element connected to the first knob element.

The first knob element, in one embodiment, is not supported on the housing portion. Since forces and loads primarily act onto the second, external knob element, no specific seating of the first knob element on the housing portion is required, hence allowing for a simple construction and connection of the first knob element to the control element.

A user may actuate the second knob element by rotating the second knob element about the axis of rotation in order to transfer a rotational movement to the first knob element and via the first knob element to the control element and/or by pushing onto the second knob element in order to transfer a translational movement onto the first knob element and via the first knob element to the control element. To transfer a rotational movement from the second knob element to the first knob element, herein, the first knob element and the second knob element are in operative connection such that a rotation of the second knob element causes the first knob element to be carried along and to be rotated correspondingly. The operative connection may for example be established by an engagement element arranged on one of the first knob element and the second knob element interacting with an engagement opening arranged on the other of the first knob element and the second knob element. The engagement element, for example having the shape of a radially extending pin, engages with the engagement opening such that a rotation of the second knob element causes the first knob element to be carried along and to be rotated, the rotational movement being transferred from the first knob element to the control element by the operative connection between the first knob element and the control element.

The idea of the invention shall subsequently be described in more detail with reference to the embodiments shown in the figures. Herein:

FIG. 2 shows a view of a medical device having an actuation element;

FIG. 3 shows a view of the medical device when actuating the actuation element;

FIG. 4 shows a view of the medical device, in an open state of a closure element in the shape of a door on which the actuation element is placed;

FIG. 8 shows a view of the medical device, with the internal knob element being detached from a control element of the medical device; and FIG. 9 shows a schematic view of the operative connection of the external knob element, the internal knob element and the control element to each other.

Figure 1:
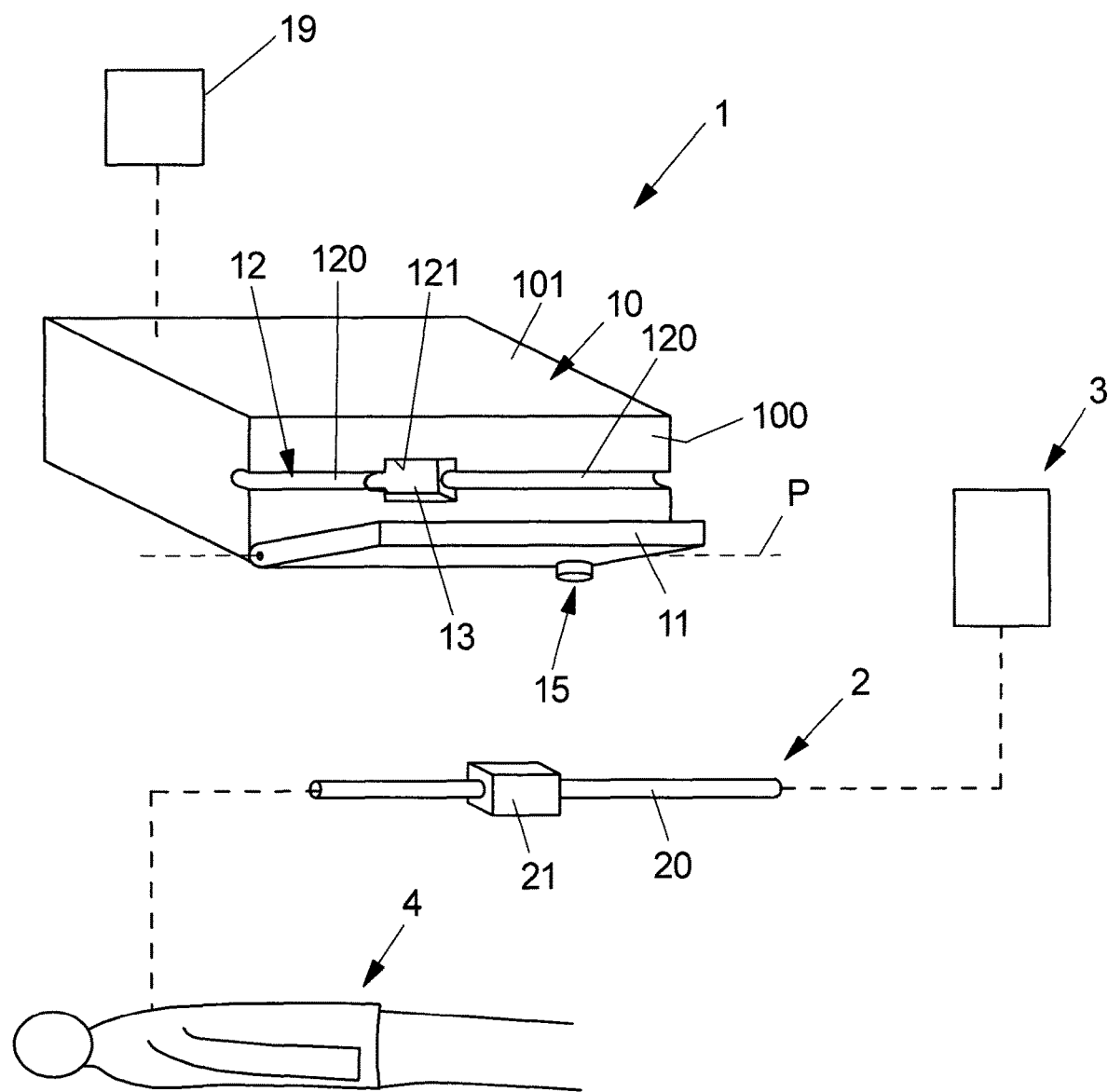
FIG. 1 shows a schematic view of a medical device in the shape of an infusion pump.
Figure 5:
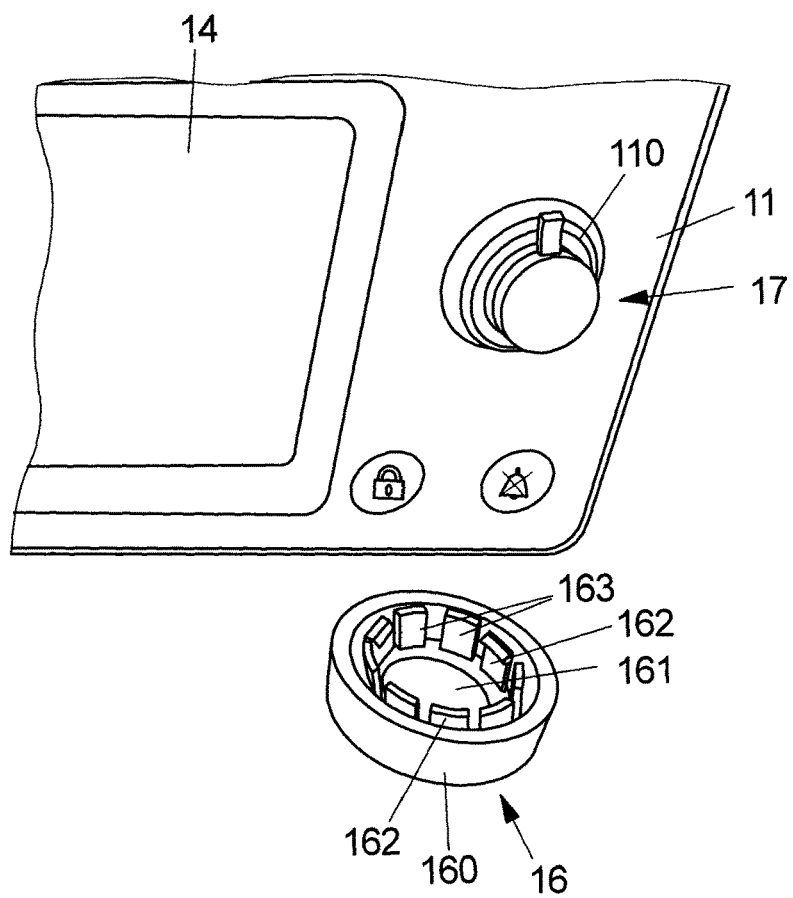
FIG. 5 shows a view of the medical device, with an external knob element being detached from an internal knob element of the actuation element.
Figure 6:
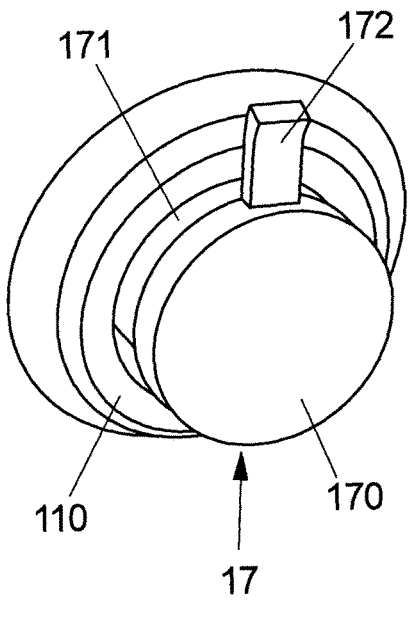
FIG. 6 shows an enlarged view of the internal knob element.

FIG. 1 shows a schematic view of a medical device 1 in the shape of an infusion device, for example a volumetric (peristaltic) infusion pump serving to administer a medical fluid from a container 3 via a pumpset 2 towards a patient 4.

The medical device 1, in the embodiment of FIG. 1, comprises a housing 10 having a housing body 101. On a front face 100 of the housing body 101 a receptacle 12 is formed, the receptacle 12 comprising first portions 120 for receiving line sections 20 of the pumpset 2 and a second portion 121 being shaped to for example receive a pump module 21 of the pumpset 2. Once received in the receptacle 12, a pumping mechanism 13 of the medical device 1 may act onto the pumpset 2 for causing a medical fluid to flow through the pumpset 2 from the container 3 towards the patient 4 such that a medical fluid may be delivered from the container 3 to the patient 4.

A housing portion 11 in the shape of a closure element is pivotably connected to the housing body 101 about a pivot axis P. The housing portion 11 in the shape of the closure element may be pivoted with respect to the housing body 101 in order to allow a user to access the receptacle 12 at the front face 100 of the housing body 101 and to place a pumpset 2 in the receptacle 12. Once a pumpset 2 is placed in the receptacle 12, the housing portion 11 in the shape of the closure element is closed such that the medical device 1 may be brought into a condition ready for operation.

The medical device 1 comprises a control device 19 serving to control operation of the medical device 1, for example to control the operation of the pumping mechanism 13 and/or to control communication with other medical devices 1, an external control system or a hospital information system (HIS).

In the embodiment of FIG. 1, an actuation element 15 is placed on the housing portion 11 in the shape of the closure element, the actuation element 15 allowing a user to enter input commands to the control device 19.

An embodiment of the actuation element 15 is shown in different views in FIGS. 2 to 9.

The actuation element 15, in the illustrated embodiment, comprises a first, internal knob element 17 connected to a control element 18 in the shape of a pin placed on the housing portion 11. The control element 18 can be rotated about an axis of rotation R (rotation action A in FIG. 9) and can be pushed to be linearly moved along the axis of rotation R (pushing action B in FIG. 9). By actuating the control element 18 control commands may be entered into the system and may be issued to the control device 19, for example to scroll through a menu displayed on a display device 14 of the housing portion 11 or to choose and confirm a specific input option, for example a menu entry, displayed on the display device 14.

The actuation element 15 furthermore comprises a second, external knob element 16 which is accessible by a user and which can be actuated by the user in order to actuate the control element 18.

The second, external knob element 16 is seated and supported on the housing portion 11, but can be rotated with respect to the housing portion 11 about the axis of rotation R. The second, external knob element 16 comprises an edge portion 160 formed by an outer cylindrical wall of the second, external knob element 16, the edge portion 160 being in axial abutment with the housing portion 11, as this is visible from the schematic drawing of FIG. 9. The second, external knob element 16 hence is supported along the axis of rotation R with respect to the housing portion 11.

The second, external knob element 16 comprises a group of locking elements 162 placed radially within the edge portion 160 and axially protruding with respect to a central push portion 161 along the axis of rotation R. The locking elements 162, in the shape of elastically deformable fingers, each carry a locking nose 165 and, by means of the locking nose 165, are in positive locking engagement with a rim section 111 of a fixation member 110 integrally formed on the housing portion 11. The fixation member 110 axially protrudes, with a wall section 112, from the housing portion 11, the rim section 111 circumferentially extending about the wall section 112 and radially protruding from the wall section 112 in order to establish the positive locking connection in between the second, external knob element 16 and the housing portion 11, as visible from FIG. 9.

Figure 7:
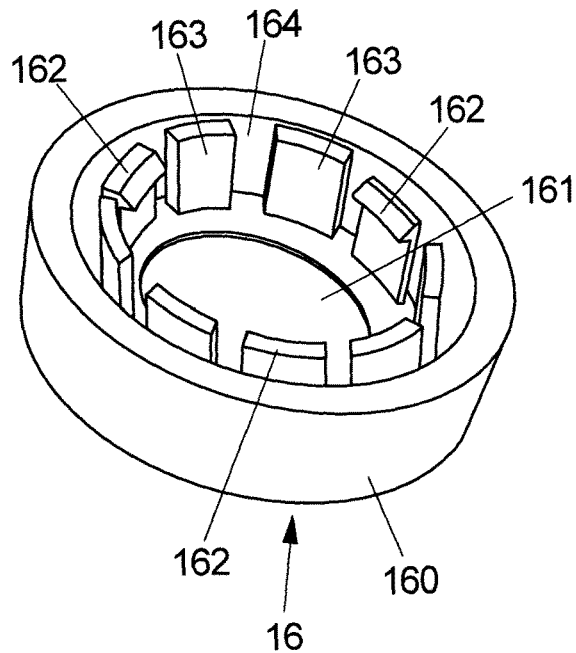
FIG. 7 shows an enlarged view of the external knob element.

The group of locking elements 162 is aligned along a circle extending circumferentially about the axis of rotation R, as this is visible for example from FIG. 7. By means of the locking elements 162 the second, external knob element 16 hence is held on the housing portion 11 such that the second, external knob element 16 can be rotated with respect to the housing portion 11, but is supported with respect to the housing portion 11 along the axis of rotation R (by means of the abutment of the edge portion 160 with the housing portion 11) and in a plane transverse to the axis of rotation R (by means of the locking elements 162).

As visible from FIG. 7, the second, external knob element 16 comprises a pair of carrier elements 163 in addition to the locking elements 162, the carrier elements 163 being placed in between two locking elements 162 and forming an engagement opening 164 in between.

The first, internal knob element 17 comprises a head portion 170 received within the second, external knob element 16, as visible from FIG. 8, and a shaft portion 171 axially extending from the head portion 170. Centrally within the shaft portion 171 a coupling opening 173 is formed by means of which the first, internal knob element 17 is placed on the control element 18 and hence is operatively connected with the control element 18, as this is shown in FIG. 9, such that a rotational action A as well as a push action B exerted on the first, internal knob element 17 is transferred to a corresponding motion of the control element 18 to issue a control command for the control device 19 linked to the control element 18, as schematically indicated in FIG. 9.

The head portion 170 is received radially in between the locking elements 162 of the second, external knob element 16 with a play when viewed in a plane transverse to the axis of rotation R, as visible from FIG. 9. Forces F1 acting onto the second, external knob element 16 in a direction transverse to the axis of rotation R hence are not transferred from the second, external knob element 16 to the first, internal knob element 17 and onto the control element 18.

Furthermore, forces F2 acting axially along the axis of rotation R onto the edge portion 160 are transferred, by means of the abutment of the edge portion 160 on the housing portion 11, to the housing portion 11, but are not introduced into the first, internal knob element 17 and hence not into the control element 18. Hence, forces acting onto the actuation element 15 for example when the housing portion 11 in the shape of the closure element is opened, as visible in FIG. 4, do not cause excessive loads on the first, internal knob element 17 and the control element 18, hence preventing a damage on the control element 18.

The second, external knob element 16 is formed flexible at its central push portion 161 such that a user may press on the push portion 161 in order to cause a pushing action B on the first, internal knob element 17 and the control element 18, as this is visible from FIG. 3 and FIG. 9. A user hence may press centrally on the second, external knob element 16 to cause a linear movement of the control element 18 along the axis of rotation R for actuating the control element 18.

The first, internal knob element 17 comprises, radially protruding from the head portion 170, an engagement element 172 which is in engagement with the engagement opening 164 formed in between the carrier elements 163 within the second, external knob element 16. Hence, a rotational movement of the second, external knob element 16 causes the first, internal knob element 17 to be carried along such that the control element 18 is rotated about the axis of rotation R and hence is actuated by rotational movement (rotation action A indicated in FIG. 9).

The first, internal knob element 17 hence is rotated together with the second, external knob element 16 upon a rotation action A at the second, external knob element 16, the rotational coupling however not causing transverse load forces F1 or axial load forces F2 to be transferred onto the first, internal knob element 17 and the control element 18.

Because the actuation element 15 comprises two separate parts which—with respect to load forces F1, F2 acting onto the second, external knob element 16—are effectively decoupled from each other, such that a transfer of load forces F1, F2 to the control element 18 is effectively prevented. Only actuation movements A, B are transferred from the second, external knob element 16 via the first, internal knob element 17 to the control element 18, hence preventing the control element 18 to be damaged in case of excessive loads acting onto the second, external knob element 16.

The second, external knob element 16 may for example be integrally formed by an injection molding technique, for example a two-component injection molding technique. In this regard, the central section representing the push portion 161 may be formed from a flexible, soft material allowing a user to depress the push portion 161 in order to exert a pushing action B on the first, internal knob element 17 and the control element 18.

The idea of the invention is not limited to the embodiments described above, but may be implemented in an entirely different fashion.

An actuation element of the type described herein may be used on any medical device such as an infusion device or any other device used in the context of administering a medical fluid to a patient, for example a control device (such as an infusion manager) or the like.

The actuation element may allow for a pushing action as well as a rotational actuation, wherein it also is conceivable that the actuation element may be actuated by either pushing or rotation, but not both.

LIST OF REFERENCE NUMERALS

1 Infusion device
10 Housing
100 Front face
101 Housing body
11 Housing portion (closure element)
110 Fixation member
111 Rim section
112 Wall portion
12 Receptacle
120, 121 Portion
13 Pumping mechanism
14 Display device
15 Actuation element
16 Knob element
160 Edge portion
161 Push portion
162 Locking elements
163 Carrier elements
164 Engagement opening
165 Locking nose
17 Knob element
170 Head portion
171 Shaft portion
172 Engagement element
173 Coupling opening
18 Control element 19 Control device
2 Pumpset
20 Line section
21 Pump module
3 Container
4 Patient
A Rotation action
B Push action
F1, F2 Forces
P Pivot axis
R Axis of rotation

The invention claimed is:

1. A medical device for administering a medical fluid to a patient, the medical device comprising:
a housing comprising a housing portion,
a control device for controlling operation of the medical device,
a control element placed on said housing portion and being actuatable for entering a control command to be input to the control device, wherein the control element, for actuation, is at least one of rotatable about an axis of rotation and linearly movable along the axis of rotation with respect to said housing portion, and
an actuation element operatively connected to the control element for actuating the control element,
wherein the actuation element comprises a first knob element operatively connected to the control element and a physically separate second knob element supported directly on said housing portion, the second knob element surrounding the first knob element with the first knob element completely inside the second knob element, wherein the second knob element is user actuatable and operatively connected to the first knob element such that a user action is transferred to the first knob element and via the first knob element to the control element for actuating the control element.

2. The medical device according to claim 1, wherein the second knob element is rotatably mounted on the housing portion.

3. The medical device according to claim 1, wherein the second knob element comprises at least one locking element connected, by means of a positive locking connection, to a fixation member arranged on the housing portion.

4. The medical device according to claim 3, wherein the at least one locking element comprises a group of locking elements arranged along a circle circumferentially extending about the axis of rotation, the first knob element being received radially inside the group of locking elements.

5. The medical device according to claim 3, wherein the fixation member extends circumferentially about the control element.

6. The medical device according to claim 3, wherein the fixation member is integrally connected to the housing portion.

7. The medical device according to claim 3, wherein the fixation member comprises a wall portion axially protruding from the housing portion and a rim section radially protruding with respect to the wall portion, the at least one locking element engaging with the rim section.

8. The medical device according to claim 1, wherein the second knob element comprises an edge portion which is in abutment with the housing portion along the axis of rotation.

9. The medical device according to claim 1, wherein the second knob element comprises a push portion which is pushable for acting onto the first knob element for linearly moving the control element along the axis of rotation.

10. The medical device according to claim 9, wherein the second knob element, at the push portion, is formed flexible.

11. The medical device according to claim 1, wherein the first knob element is operatively connected to the control element such that at least one of a rotational movement about the axis of rotation and a linear movement along the axis of rotation by the first knob element is transferred to the control element to cause a corresponding movement of the control element.

12. The medical device according to claim 1, wherein the first knob element comprises a head portion and a shaft portion extending from the head portion along the axis of rotation, wherein the shaft portion is operatively connected to the control element and the head portion is operatively connected to the second knob element.

13. The medical device according to claim 12, wherein the head portion, in a plane transverse to the axis of rotation, is arranged with a play with respect to the second knob element.

14. The medical device according to claim 1, wherein the first knob element is not supported on the housing portion.

15. The medical device according to claim 1, wherein one of the first knob element and the second knob element comprises an engagement element, and the other of the first knob element and the second knob element comprises an engagement opening, the engagement element engaging with the engagement opening such that a rotational movement of the second knob element causes a corresponding rotational movement of the first knob element.

16. The medical device according to claim 1, wherein the second knob element is in axial abutment with the housing portion along the axis of rotation, the axial abutment preventing motion of the second knob at the axial abutment in a pushing state.

17. The medical device according to claim 16, wherein the second knob element comprises a push portion which is pushable for acting onto the first knob element for linearly moving the control element along the axis of rotation.

18. The medical device according to claim 1, wherein the second knob element comprises an edge that is in abutment with the housing portion circumferentially about the first knob element, the abutment of the edge with the housing portion prevents motion of the edge relative to the housing portion along the axis of rotation in a state where the second knob element is pushed along the axis of rotation toward the housing.

19. The medical device according to claim 18, wherein the second knob element comprises a push portion which is pushable along the axis of rotation toward the housing to linearly move the control element via the first knob element along the axis of rotation.

* * * * *